United States Patent
Fang et al.

(10) Patent No.: US 12,234,934 B2
(45) Date of Patent: Feb. 25, 2025

(54) TUBING JUNCTION ASSEMBLY

(71) Applicant: CareFusion 303, Inc., San Diego, CA (US)

(72) Inventors: Yan Fang, Irvine, CA (US); Aaron Wang, Laguna Hills, CA (US); Siddarth Shevgoor, Mission Viejo, CA (US)

(73) Assignee: CAREFUSION 303, INC., San Diego, CA (US)

( * ) Notice: Subject to any disclaimer, the term of this patent is extended or adjusted under 35 U.S.C. 154(b) by 112 days.

(21) Appl. No.: 18/174,047

(22) Filed: Feb. 24, 2023

(65) Prior Publication Data

US 2023/0304615 A1    Sep. 28, 2023

Related U.S. Application Data

(60) Provisional application No. 63/323,433, filed on Mar. 24, 2022.

(51) Int. Cl.
| | |
|---|---|
| F16L 33/34 | (2006.01) |
| A61M 39/12 | (2006.01) |
| F16L 11/06 | (2006.01) |
| F16L 33/207 | (2006.01) |
| F16L 33/22 | (2006.01) |
| F16L 33/28 | (2006.01) |
| F16L 47/04 | (2006.01) |

(52) U.S. Cl.
CPC ........... *F16L 33/34* (2013.01); *F16L 33/2071* (2013.01); *F16L 33/28* (2013.01); *A61M 39/12* (2013.01); *F16L 11/06* (2013.01); *F16L 33/225* (2013.01); *F16L 47/041* (2019.08)

(58) Field of Classification Search
CPC ......... F16L 33/34; F16L 33/28; F16L 33/225; F16L 33/226; F16L 47/041; A61M 2039/1027; A61M 39/12; A61M 39/20
See application file for complete search history.

(56) References Cited

U.S. PATENT DOCUMENTS

| | | | | |
|---|---|---|---|---|
| 2,319,024 | A | * | 5/1943 | Wehringer ............ F16L 33/225 |
| 3,269,756 | A | * | 8/1966 | Bloom .................. F16L 47/041 |
| 3,408,098 | A | * | 10/1968 | Wilson .................. F16L 47/041 |

(Continued)

OTHER PUBLICATIONS

International Search Report and Written Opinion for Application No. PCT/US2023/013843, dated Jun. 7, 2023, 14 pages.

*Primary Examiner* — William S. Choi
(74) *Attorney, Agent, or Firm* — Morgan, Lewis & Bockius LLP

(57) ABSTRACT

A tubing junction assembly may include a body, and a collar coupled to the body. The body may include a head portion, a base portion, and an intermediate portion. At least a portion of an outer surface of the body at the intermediate portion may define a cross-sectional width that tapers from the head portion to the base portion. The collar may have an inner surface defining a passage. A tubing may be stretched over the outer surface of the body with a proximal end portion of the tubing stretched over at least a portion of the outer surface of the body at the intermediate portion. The inner surface of the collar may be sleeved over a portion of the outer surface of the tubing and coupled to the collar such that the proximal end portion of the tubing is sandwiched and compressed between the body and the collar.

19 Claims, 5 Drawing Sheets

(56) References Cited

U.S. PATENT DOCUMENTS

| | | | | |
|---|---|---|---|---|
| 3,710,428 | A * | 1/1973 | Bjalme | F16L 33/28 |
| 4,029,345 | A * | 6/1977 | Romanelli | F16L 47/041 |
| 4,114,930 | A * | 9/1978 | Perkins | |
| 5,578,059 | A * | 11/1996 | Patzer | |
| 5,637,102 | A | 6/1997 | Tolkoff et al. | |
| 6,003,906 | A * | 12/1999 | Fogarty | F16L 33/225 |
| 2006/0089603 | A1* | 4/2006 | Truitt | |
| 2015/0362109 | A1 | 12/2015 | Buchanan | |
| 2017/0138518 | A1* | 5/2017 | Blake | F16L 33/225 |
| 2017/0290216 | A1* | 10/2017 | Truitt | |
| 2021/0138214 | A1* | 5/2021 | Davidson | |
| 2022/0065373 | A1 | 3/2022 | Suwito | |

\* cited by examiner

TUBING JUNCTION ASSEMBLY

CROSS-REFERENCE TO RELATED APPLICATIONS

This application claims the benefit of U.S. Provisional Application No. 63/323,433, titled "TUBING JUNCTION ASSEMBLY," filed Mar. 24, 2022, the disclosure of which is incorporated herein by reference in its entirety.

BACKGROUND

The present disclosure relates generally to coupling tubing with another apparatus in a medical system, and more particularly, to fluidly coupling tubing with another apparatus in a medical system using a mechanical junction and without requiring adhesive, welding, or the similar bonding methods.

In the medical field, as well as in other fields and applications, tubing can be coupled with an apparatus or a fitting and used to transfer a fluid. In the medical field, patients can often be provided with medical fluids that are administered through intravenous (IV) infusion using assemblies of tubes and fittings commonly referred to as "IV sets." IV sets are produced in a variety of configurations with various types of access ports, manifolds, valves, drip chambers, and other fittings connected by lengths of medical tubing.

The connections between the tubing and a fitting can be referred to as a "joint" or a "junction." When the assembly of tubing and fitting are used in a medical application, or other applications requiring a high degree of integrity or performance, it is important to prevent the defects in the junction between the tubing and the fitting. It is also important to reduce the required steps for preparation and assembly of the junction during manufacturing.

A defect in the junction between the tubing and the fitting could result in a leakage passage between the fluid passage of the assembly and an environment outside of the fluid path. The leakage path may cause the medical fluid to exit the assembly or could permit air to enter the assembly, which could result in inadequate delivery of fluid and or medicament to the patient, the interaction of a gas the assembly, and/or could compromise the sterility of the assembly or medicament.

The junction can be achieved by bonding the tubing and the fitting together, such as by using a solvent, adhesive, welding, or the like. The junction can also be achieved by using a mechanical coupling, such as an interference fit it or a clamp. However, a variety of factors for coupling the tubing and fitting together must be considered to prevent the formation of a defect in the junction.

SUMMARY

The present Application provides tubing junction assemblies comprising a body including a head portion, and a base portion extending longitudinally from the head portion, the body having an outer surface, a proximal end portion, a distal end portion and an intermediate portion interposed between the proximal end portion and the distal end portion, wherein at least a portion of the outer surface of the body at the intermediate portion defines a cross-sectional width that tapers from the head portion to the base portion; and a collar coupled to the body, the collar having a head portion, a base portion extending longitudinally from the head portion, and an inner surface defining a passage that that extends between the head portion and the base portion, the head portion comprising a proximal end portion and a distal end portion, wherein the inner surface at the head portion of the collar defines a cross-sectional width that tapers from the proximal end portion to the distal end portion of the head portion, wherein a tubing having a proximal end portion, a distal end portion, an outer surface, and an inner surface defining a lumen extending from the proximal end portion to the distal end portion is stretched over the outer surface of the body with the proximal end portion of the tubing stretched over at least a portion of the outer surface of the body at the intermediate portion, and wherein the inner surface of the collar is sleeved over at least a portion of the outer surface of the tubing and coupled to the collar such that the proximal end portion of the tubing is sandwiched and compressed between the body and the collar.

In some instances, the present disclosure provides methods of forming a tubing junction assembly, the method comprising providing a body including a head portion, a base portion extending longitudinally from the head portion, the body having an outer surface, a proximal end portion, a distal end portion and an intermediate portion interposed between the proximal end portion and the distal end portion, wherein at least a portion of the outer surface of the body at the intermediate portion defines a cross-sectional width that tapers from the head portion to the base portion; sleeving a tubing over the outer surface of the body and stretching a proximal end portion of the tubing over at least a portion of the outer surface of the body at the intermediate portion to form at least one of a y-shape or an umbrella-shape; sleeving a collar over the tubing such that the tubing is interposed between the collar and the body, the collar having a head portion, a base portion extending longitudinally from the base portion, and an inner surface defining a passage that extends between the head portion and the base portion; and connecting a lower surface of the head portion of the body to an upper surface of the of the head portion of the collar such that a proximal end of the y-shape or umbrella-shape proximal end portion tubing is sandwiched and compressed between the body and the collar.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the inventions are described below with reference to the drawings. The illustrated embodiments are intended to illustrate, but not to limit, the inventions. The drawings contain the following figures.

DETAILED DESCRIPTION

Figure 1:
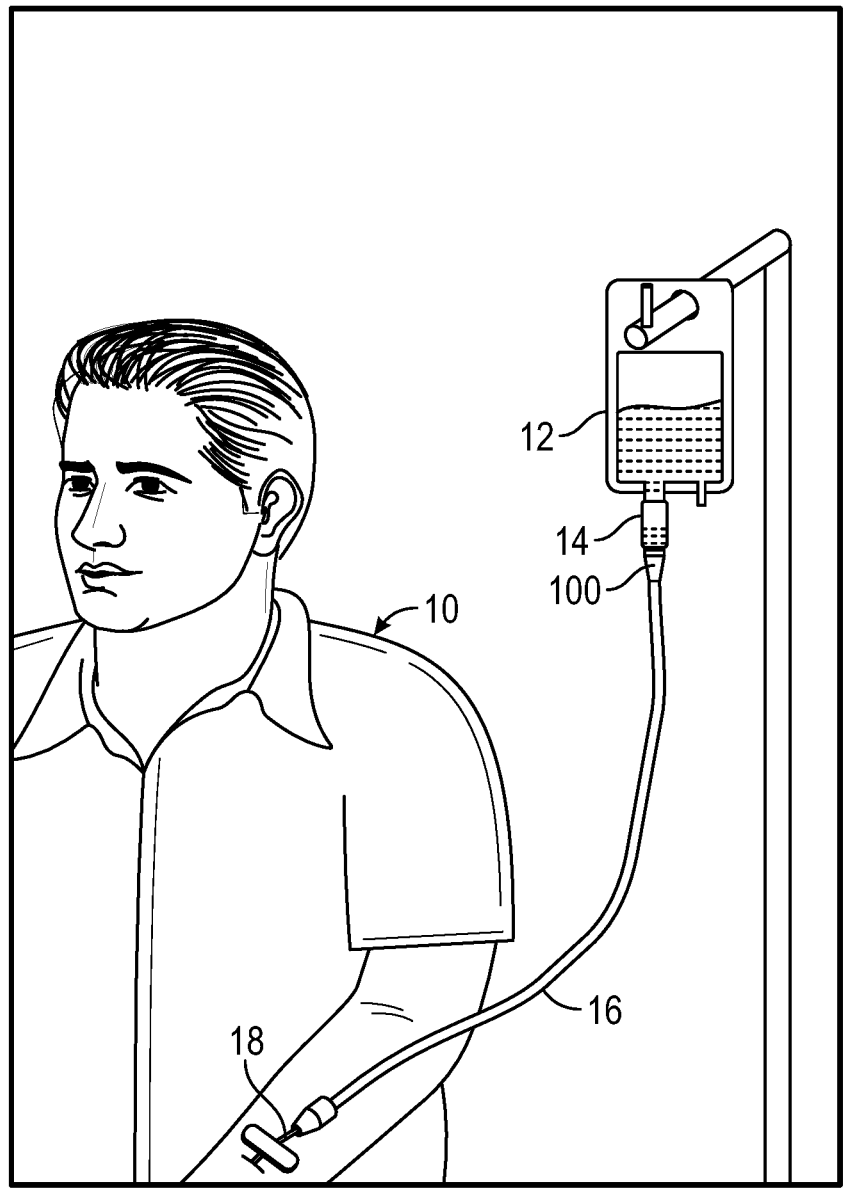
FIG. 1 illustrates a tubing junction assembly incorporated into an IV set coupled to a patient, in accordance with aspects of the present disclosure.

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present description sets forth specific details of various embodiments, it will be appreciated that the description is illustrative only and should not be construed in any way as limiting. Additionally, it is contemplated that although particular embodiments of the present inventions may be disclosed or shown in the context of an apparatus in a medical system, such embodiments can be used in other fluid transfer applications (such as the movement of food, beverages, fuel, lubrication, etc.). Furthermore, various applications of such embodiments and modifications thereto, which may occur to those who are skilled in the art, are also encompassed by the general concepts described herein.

In accordance with some embodiments, the present application discloses various features and advantages of a tubing junction assembly. The tubing junction assembly can be used to reliably and easily couple an end portion of tubing to another apparatus or device and permit the movement of a fluid therebetween. Further, the tubing junction assembly can provide an effective and reliable coupling between tubing and an apparatus that is comparable to or exceeds other methods such as solvent bonding. The tubing junction assembly of the present disclosure minimizes and/or eliminates factors that could reduce the reliability and performance of the junction and also reduces the complexity of assembling the junction.

For example, the tubing junction assembly of the present disclosure provides a junction between tubing and an apparatus without requiring a specific volume of adhesive or solvent to be applied to a specific length of the tubing. The tubing junction assembly also does not require chemical compatibility of the material for each of the adhesive or solvent, tubing, and the apparatus for the coupling to be effective and reliable. Additionally, the tubing junction assembly can achieve an effective and reliable coupling with a greater degree of tolerance between the tubing and the apparatus. The simple and effective features of the present disclosure provide a tubing junction assembly that can be easily adapted to automated manufacturing or assembly operations.

The tubing junction assembly of the present disclosure includes, but is not limited to, a body and a collar, where the collar and body can be coupled together to engage against a portion of tubing flared, swaged, or otherwise stretched onto a widened portion of the body and sandwiched between the body and collar. Although the body and the collar are described or illustrated in isolation, it should be understood that any of portion of the body and/or collar can be configured as a portion of another device or apparatus. For example, the body can be a portion of an IV bag, a drip chamber, a check valve, a flow controller, a fluid filter, a pump, or another apparatus or device.

Referring now to the figures, FIG. 1 illustrates an example of a tubing junction assembly 100 in use in accordance with aspects of the present disclosure. The tubing junction assembly 100 is fluidly coupled with tubing 160 of an intravenous (IV) set being used to deliver a fluid to a patient 10. The IV set includes a medicament bag 12, a drip chamber 14, tubing 16, the tubing junction assembly 100, and an IV catheter 18. Although the illustrated embodiment of the tubing junction assembly 100 is coupled with the drip chamber 14, it should be understood that the tubing junction assembly 100 of the present disclosure can be incorporated into or coupled to other apparatus and devices, such as a manifold, a needleless access port, a check valve, a drip chamber, or other fluid transfer and/or control devices. Further, the tubing junction assembly of the present disclosure can be incorporated into or coupled to apparatus and devices used in other applications or industries other than medicine, including, for example, food, petroleum, nuclear utilities, transportation, mining, pulp and paper, steel, marine, aviation, construction, and other industries.

Figure 2:
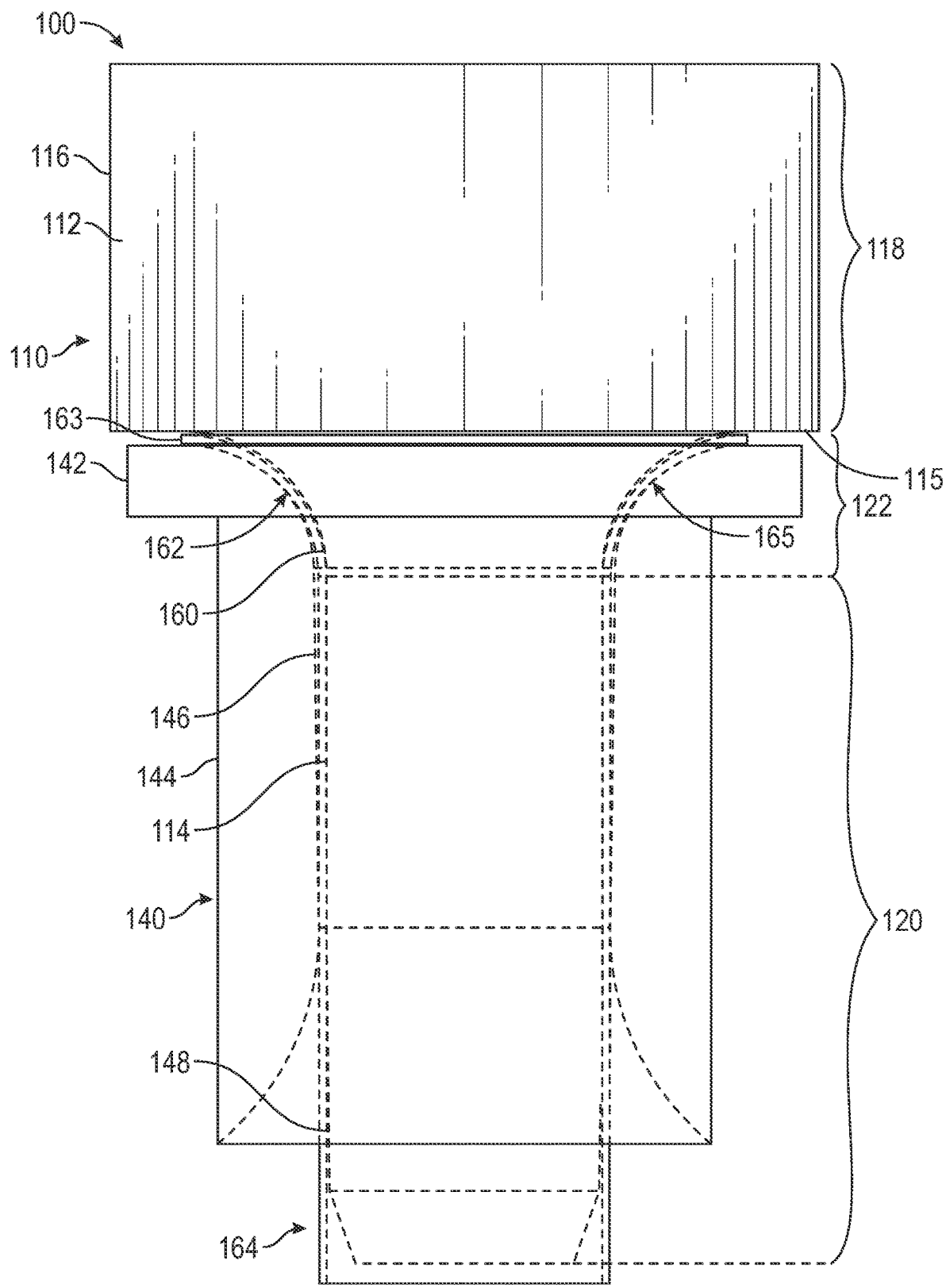
FIG. 2 illustrates a planar view of a tubing junction assembly, in accordance with aspects of the present disclosure.
Figure 3:
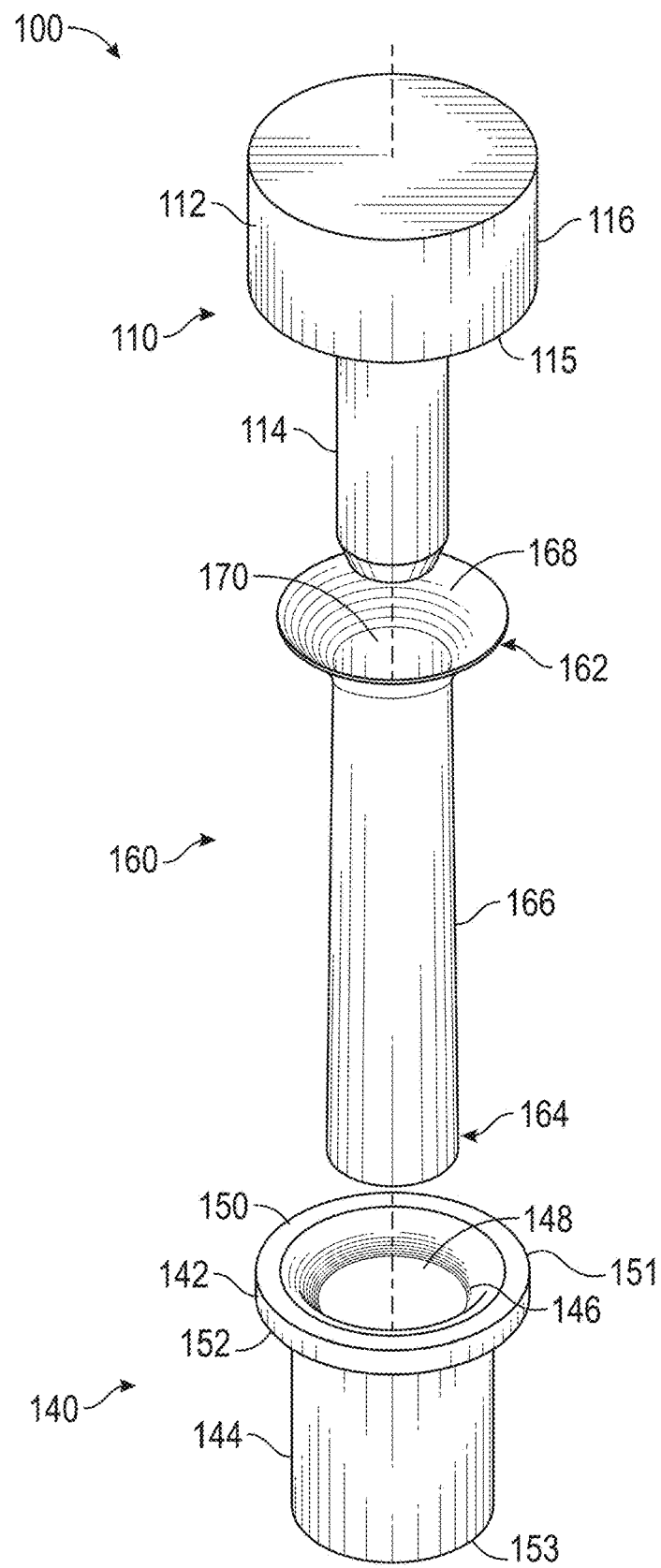
FIG. 3 illustrates an exploded perspective view of the tubing junction assembly of FIG. 2, in accordance with aspects of the present disclosure.
Figure 4:
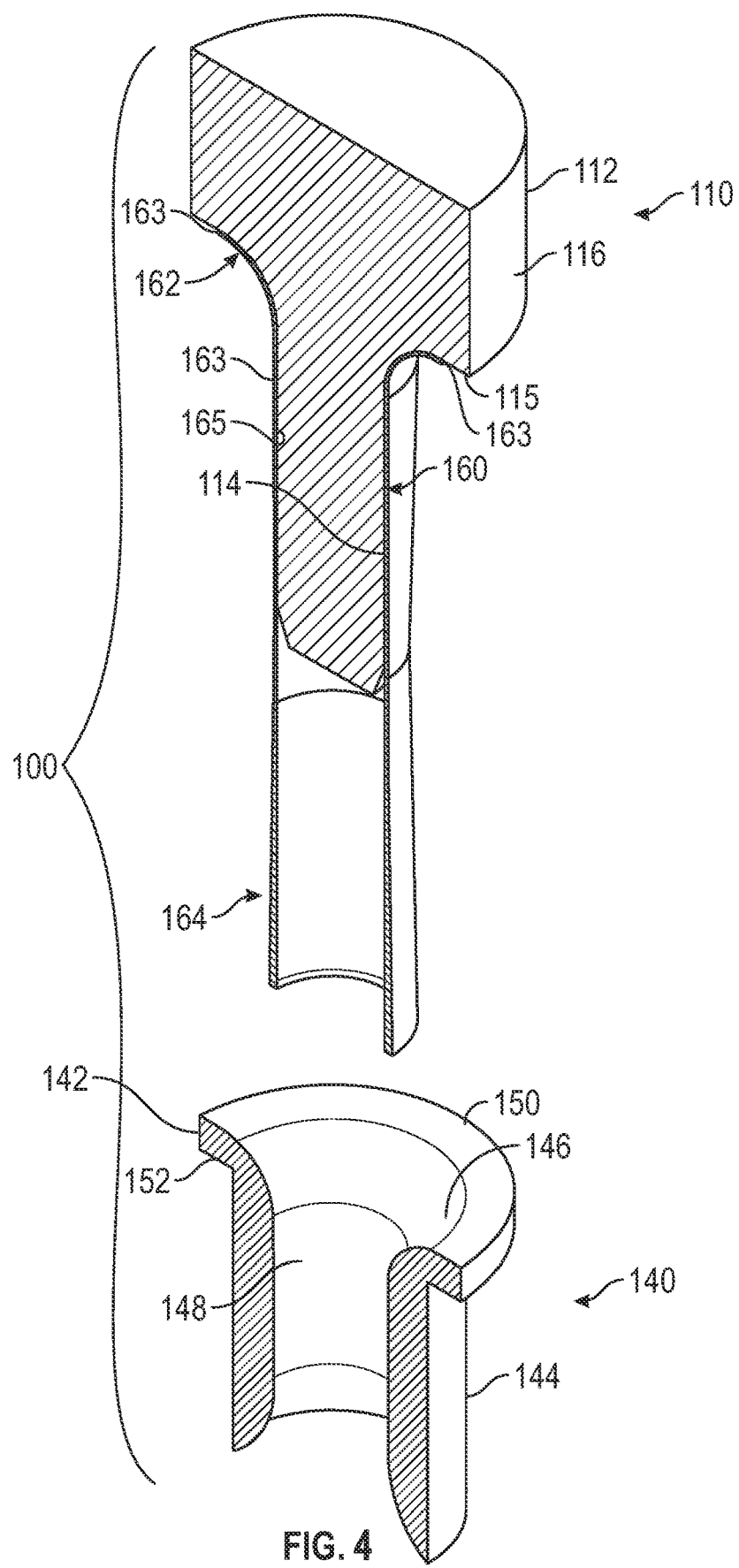
FIG. 4 illustrates a cross-sectional perspective view of the tubing junction assembly of FIG. 2, with a collar of the tubing junction assembly removed, in accordance with aspects of the present disclosure.

FIG. 2 illustrates a planar view of a tubing junction assembly 100, in accordance with aspects of the present disclosure. FIG. 3 illustrates an exploded perspective view of the tubing junction assembly 100 of FIG. 2, in accordance with aspects of the present disclosure. FIG. 4 illustrates a cross-sectional perspective view of the tubing junction assembly 100 of FIG. 2, with a collar 140 of the tubing junction assembly removed, in accordance with aspects of the present disclosure. According to various embodiments of the present disclosure, the tubing junction assembly 100 may be assembled by moving the collar 140 onto a portion of the body 110, with a proximal end portion 162 of the tubing 160 flared, swaged, or otherwise stretched over a lower surface 115 of a head portion 112 of the body 110 (also referred to herein as the intermediate portion 122 of the body 110). As shall be described in further detail below, when the proximal end portion 162 also referred to herein as an umbrella shape, umbrella-shaped portion, or y-shape, y-shaped portion of the tubing 160 is flared, swaged, or otherwise stretched over the intermediate portion of the body 110 and the collar 140 is sleeved over the tubing 160 and coupled to the lower surface 115 of the head portion with the proximal end portion 162 of the tubing interposed therebetween, the tubing is not only compressed radially inward between the outer surface 116 of the body 110 and the inner surface 146 of collar 140, but is additionally axially compressed between the lower surface 115 of the head portion 112 and the upper surface 150 of the head portion 142 of the collar. When the proximal end portion 162 of the tubing 160 has an umbrella or y-shape, the cross-sectional diameter or width of the tubing 160 along the proximal end portion 162 increases in a direction away from the distal end portion 164 of the tubing.

As depicted in FIG. 2, with continued reference to FIGS. 3 and 4 in some embodiments, the tubing junction assembly 100 may include the body 110 including a head portion 112, and a base portion 114 extending longitudinally from the head portion 112. The body 110 may have an outer surface 116, a proximal end portion 118, a distal end portion 120, and an intermediate portion 122 interposed between the proximal end portion 118 and the distal end portion 120. At least a portion of the outer surface 116 of the body 110 at the intermediate portion 122 may define a cross-sectional width that tapers from the head portion 112 to the base portion 114.

It is contemplated that the proximal end portion 118 of the body may form another component such as another apparatus or device. For example, the proximal end portion 118 of the body 110 may be unitarily molded as another component. In another example, the proximal end portion 118 of the body 110 may be coupled with another component by applying an adhesive or welding to the component. In yet another example, the body 110 can be coupled with another component using a mechanical fastener, such as complementary threads, a latch, a clamp, or another of fastening the body to the component 20. As such, to simplify illustration of the features of the present disclosure, the body 110 may be described as being coupled with or being part of an IV bag, a drip chamber, a check valve, a flow controller, a fluid filter, a pump, or another apparatus or device.

According to various embodiments of the present disclosure, the tubing junction assembly may further include collar 140 coupled to the body 110. As depicted, the collar 140 may have a head portion 142, a base portion 144 extending longitudinally from the head portion 142, and an inner surface 146 defining a passage 148 that that extends between the head portion 142 and the base portion 144. As depicted, the passage 148 may extend through the upper surface 150 and a lower surface 155, and the passage 148 may be configured to permit the collar to be inserted over at least a portion of the body 202 and the tubing 160. The head portion 142 may include a proximal end portion 151 and a distal end portion 152. The inner surface 146 at the head portion 142 of the collar 140 may define a cross-sectional width that tapers from the proximal end portion 151 to the distal end portion 152 of the head portion 142.

To resist movement of the tubing 160 relative to the body 110, and to form a fluid-tight coupling between the tubing 160 and the body 110, the collar 140 can be coupled to the body 110. In particular, the collar 140 is configured to be coupled to the body 110 by sleeving the collar 140 over the tubing 160 and onto at least a portion of the body 110. In order to permit the collar 140 to be inserted over at least a portion of the body 110 and the tubing 160, the inner surface 146 of the collar 140 that forms the passage 148 may define a cross-sectional width that is configured to allow the tubing 160 and at least a portion of the body 110 to be inserted therethrough. In some embodiments, the inner surface 146 at the base portion 148 of the collar 140 may have a cross-sectional width approximately equal to a sum of the cross-sectional width of the outer surface 116 of the body 110 at the base portion 114 and a thickness of the tubing 160 sleeved over the outer surface 116 of the body 110 at the base portion 114 such that the collar 140 is sleeved over the outer surface 116 of the tubing 160 with an interference fit to compress the tubing 160 radially inwards. In some embodiments, the passage 148 may have a cross-sectional width that is approximately equal to a cross-sectional width of the body 110 at an opposite point when the collar 140 is coupled to the body 110. In some embodiments, the cross-sectional width of the passage 148 may decrease from the proximal end portion 151 toward the distal end portion 153 of the collar 140.

Figures 5, 6:
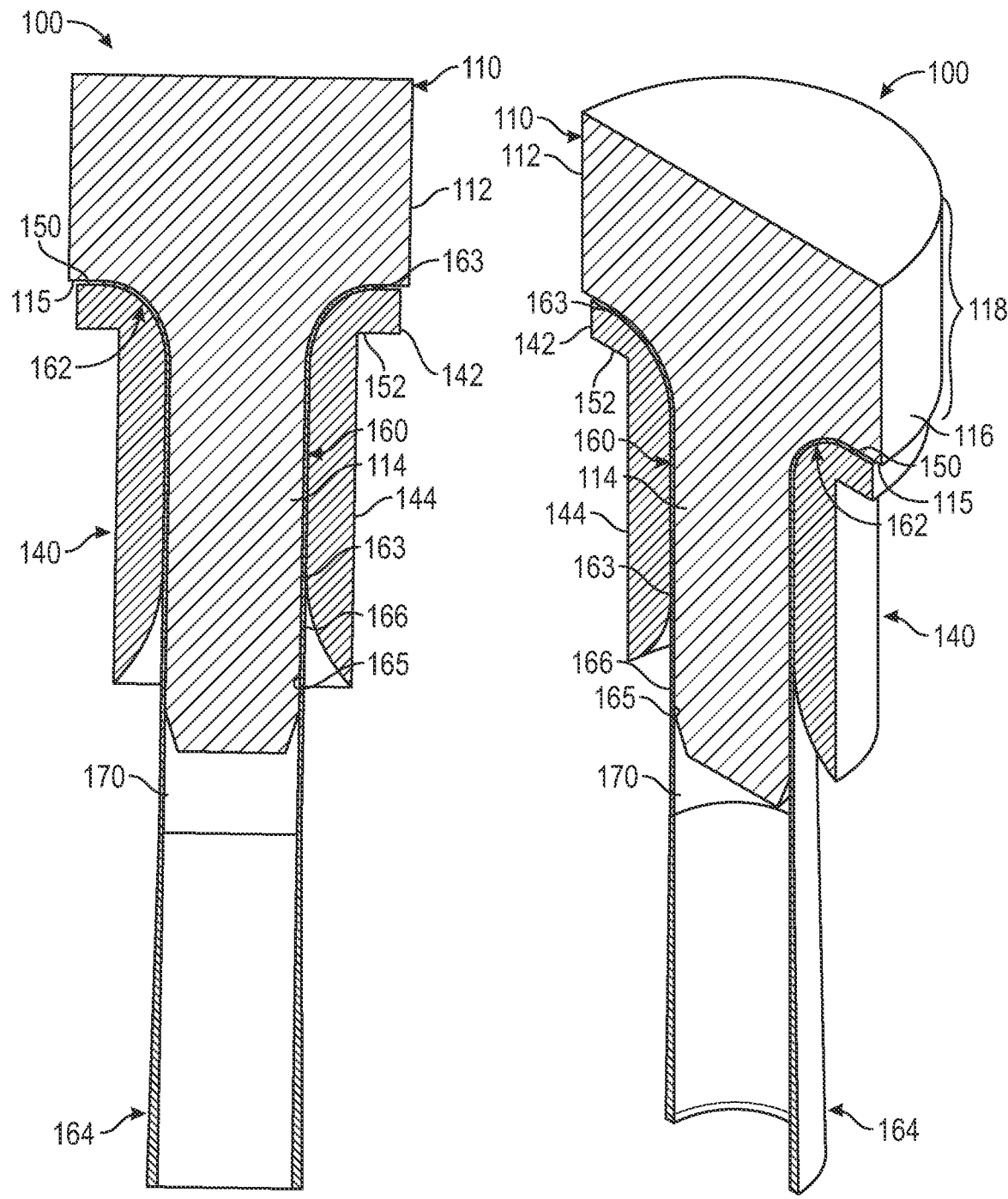
FIG. 5 illustrates a cross-sectional planar view of the tubing junction assembly of FIG. 2, in accordance with aspects of the present disclosure.
FIG. 6 illustrates a cross-sectional perspective view of the tubing junction assembly of FIG. 2, in accordance with aspects of the present disclosure

FIG. 5 illustrates a cross-sectional planar view of the tubing junction assembly 100 of FIG. 2, in accordance with aspects of the present disclosure. FIG. 6 illustrates a cross-sectional perspective view of the tubing junction assembly 100 of FIG. 2, in accordance with aspects of the present disclosure. In accordance with various embodiments of the present disclosure, the tubing 160 may have a proximal end portion 162, a distal end portion 164, an outer surface 166, and an inner surface 168 defining a lumen 170 extending from the proximal end portion 162 through the distal end portion 164. The lumen 170 of the tubing 160 may have a diameter approximately equal to the cross-sectional width of the outer surface 116 of the body 110 at the base portion 114 in an unstretched state of the tubing 160 such that the tubing 160 is sleeved over the outer surface 116 of the body 110 with an interference fit. As depicted in at least FIGS. 1 and 4, the tubing 160 may be sleeved over the outer surface 116 of the body 110 with the proximal end portion 162 of the tubing flared, swaged, or otherwise stretched over at least a portion of the outer surface 116 of the body 110 at the intermediate portion 122. In particular, in some embodiments, the stretched portion (e.g., the proximal portion 162 of the tubing), when flared, swaged, or stretched over the intermediate portion 122 of the body 110 may form at least one of a y-shape or an umbrella shape corresponding to a shape of the portion of the outer surface 162 of the body 110 at the intermediate portion 122 which defines the cross-sectional width that tapers from the head portion 112 to the base portion 114 of the body. As depicted, in order to resist movement of the tubing 160 relative to the body 110, the inner surface 168 of the collar 140 may be sleeved over at least a portion of the outer surface 116 of the tubing 160 such that the proximal end portion 162 of the tubing is sandwiched and axially compressed between an upper surface 150 of the head portion 142 of the collar 140 and a lower surface 115 of the head portion 112 of the body 110.

When the proximal end portion 162 of the tubing 160 also referred to herein as an umbrella shape, umbrella-shaped portion, or y-shape, y-shaped portion of the tubing 160 is flared, swaged, or otherwise stretched over the intermediate portion of the body 110 and the collar 140 is sleeved over the tubing 160 and coupled to the lower surface 115 of the head portion 112 with the proximal end portion 162 of the tubing interposed therebetween, the tubing is not only compressed radially inward between the outer surface 116 of the body 110 and the inner surface 146 of collar 140, but is additionally axially compressed between the lower surface 115 of the head portion 112 and the upper surface 150 of the head portion 142 of the collar. The aforementioned configuration is advantageous in that the flaring, swaging, stretching and trapping of the proximal end portion 162 of the tubing 160 also referred to herein as "umbrella swaging" adds an additional axially directioned compression force, which may increase the bond pull performance of the tubing junction assembly 100 by an additional 20%-25% over currently existing tubing junction assemblies which merely incorporate a press fit ring, which applies only a radial direction compression force—without the additional axially directioned compression force—to provide bond pull force.

In some embodiments, the tubing 160 may be a non-polyvinyl chloride (PVC) tubing. For example, in some embodiments, the tubing 160 may be a thermoplastic elastomer (TPE) tubing. In some embodiments, the tubing 160 may be a chemical-inert, solvent-inert or adhesive-inert tubing. The tubing junction assembly 100 of the various embodiments described herein is advantageous in that the extra area of the tubing which is umbrella swaged provides the additional axial direction compression force to increase bond pull performance, thereby removing the necessity of applying an adhesive or solvent to the tubing 160 in order to achieve increased bond pull performance, as commonly done with the prior art. This is advantageous as this has been proven to be the key to bond non-PVC tubing or any tubing that has nearly no reaction with solvent and/or adhesive (for example polypropylene tubing). Since the tubing junction assembly 100 of the various embodiments described herein is not limited to tubing materials that are capable of reacting with chemical/adhesive/solvent, the tubing junction assembly 100 allows for use of a larger selection of tubing materials to be used, thereby potentially decreasing costs commonly associated with tubing junction assemblies.

In accordance with various embodiments of the present disclosure, collar 140 may be coupled to the body 110 in one or more of several ways in order to axially compress the proximal portion 162 of the tubing and increase the bond pull performance of the tubing junction assembly 100. For example, in some embodiments, the upper surface 150 of head portion 142 of the collar 140 may be solvent bonded to the lower surface 115 of the head portion 112 of the body 110. In some embodiments, the upper surface 150 of head portion 142 of the collar 140 may be ultraviolet (UV) adhesive bonded to the lower surface 115 of the head portion 112 of the body 110. In some embodiments, the upper surface 150 of head portion 142 of the collar 140 is ultrasonically welded to the lower surface 115 of the head portion 112 of the body 110. In other embodiments, the upper surface 150 of head portion 142 of the collar 140 may be snap fit coupled to the lower surface 115 of the head portion 112 of the body 110. In other embodiments, the upper surface 150 of head portion 142 of the collar 140 may be threaded to the lower surface 115 of the head portion 112 of the body 110.

In some embodiments, the cross-sectional width of the inner surface 146 at the head portion 142 of the collar 140 that tapers from the proximal end portion 151 to the distal end portion 153 of the head portion 142 may be approximately equal to the cross-sectional width of outer surface 116 of the body 110 at the intermediate portion 122 that tapers from the head portion 112 to the base portion 114 of the body 110 such that the collar 140 radially compresses the stretched portion of the tubing.

In some embodiments, the cross-sectional width of the outer surface 116 of the base portion 114 of the body 110 may be approximately equal to a diameter of the lumen 170 of the tubing 160. When the base portion 114 of the body 110 is inserted into the lumen 170 of the tubing 160, and the proximal end portion 162 of the tubing 160 is moved along the outer surface 116 of the base portion 114 of body 110 toward the head portion 112, an interference fit may be established between the body 110 and the tubing 160.

According to various embodiments of the present disclosure, a method of forming the tubing junction assembly 100 may include providing the body 100 including head portion 112, base portion 114 extending longitudinally from the head portion. As discussed above, the body 110 may have outer surface 116, proximal end portion 118, distal end portion 120 and intermediate portion 122 interposed between the proximal end portion 118 and the distal end portion 120, and at least a portion of the outer surface 116 of the body 110 at the intermediate portion 122 may define a cross-sectional width that tapers from the head portion 112 to the base portion 114. The method may further include sleeving the tubing 160 over the outer surface 116 of the body 110 and flaring, swaging, or otherwise stretching the proximal end portion 162 of the tubing over at least a portion of the outer surface 116 of the body 110 at the intermediate portion 122 to form at least one of a y-shape or an umbrella-shape. The method may further include sleeving the collar 140 over the tubing 160 such that the tubing 160 is interposed between the collar 140 and the body 110. The method may further include connecting the lower surface 115 of the head portion 112 of the body 110 to the upper surface 150 of the of the head portion 142 of the collar 140 such that a proximal end of the flared, swaged, or stretched y-shape or umbrella-shape proximal end portion 162 of the tubing 160 is sandwiched and compressed between the body 110 and the collar 140.

In some embodiments, sleeving the tubing 160 over the outer surface 116 of the body 110 includes sleeving the tubing 160 over the outer surface 116 with an interference fit, and sleeving the collar 140 over the tubing 140 includes press-fitting the collar 140 over at least a portion of the tubing 160. In some embodiments, connecting the lower surface 115 of the head portion of the body 110 to the upper surface 150 of the of the head portion 142 of the collar 140 may include one or more of (i) solvent bonding the lower surface 115 of the head portion 112 of the body 110 to the upper surface 150 of the of the head portion 142 of the collar 140, (ii) ultraviolet (UV) adhesive bonding the lower surface 115 of the head portion 112 of the body 110 to the upper surface 150 of the of the head portion 142 of the collar 140, (iii) ultrasonically welding the lower surface 115 of the head portion 112 of the body 110 to the upper surface 150 of the of the head portion 142 of the collar 140, (iv) snap fitting the lower surface 115 of the head portion 112 of the body 110 to the upper surface 150 of the of the head portion 142 of the collar 140, and (v) threading the lower surface 115 of the head portion 112 of the body 110 to the upper surface 150 of the of the head portion 142 of the collar 140.

Illustration of Subject Technology as Clauses

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 5. The other clauses can be presented in a similar manner.

Clause 1: A tubing junction assembly comprising: a body including a head portion, and a base portion extending longitudinally from the head portion, the body having an outer surface, a proximal end portion, a distal end portion and an intermediate portion interposed between the proximal end portion and the distal end portion, wherein at least a portion of the outer surface of the body at the intermediate portion defines a cross-sectional width that tapers from the head portion to the base portion; and a collar coupled to the body, the collar having a head portion, a base portion extending longitudinally from the head portion, and an inner surface defining a passage that that extends between the head portion and the base portion, the head portion comprising a proximal end portion and a distal end portion, wherein the inner surface at the head portion of the collar defines a cross-sectional width that tapers from the proximal end portion to the distal end portion of the head portion, wherein a tubing having a proximal end portion, a distal end portion, an outer surface, and an inner surface defining a lumen extending from the proximal end portion to the distal end portion is stretched over the outer surface of the body with the proximal end portion of the tubing stretched over at least a portion of the outer surface of the body at the intermediate portion, and wherein the inner surface of the collar is sleeved over at least a portion of the outer surface of the tubing and coupled to the collar such that the proximal end portion of the tubing is sandwiched and compressed between the body and the collar.

Clause 2: The tubing junction assembly of Clause 1, wherein the lumen of the tubing has a diameter approximately equal to the cross-sectional width of the outer surface of the body at the base portion in an unstretched state of the tubing such that the tubing is sleeved over the outer surface of the body with an interference fit.

Clause 3: The tubing junction assembly of Clause 2, wherein the inner surface at the base portion of the collar has a cross-sectional width approximately equal to a sum of the cross-sectional width of the outer surface of the body at the base portion and a thickness of the tubing sleeved over the outer surface of the body at the base portion such that the collar is sleeved over the outer surface of the tubing with an interference fit to radially compress the tubing.

Clause 4: The tubing junction assembly of Clause 3, wherein the cross-sectional width of the inner surface at the head portion of the collar that tapers from the proximal end portion to the distal end portion of the head portion is approximately equal to the cross-sectional width of outer surface of the body at the intermediate portion that tapers from the head portion to the base portion of the body such that the collar compresses the stretched portion of the tubing.

Clause 5: The tubing junction assembly of Clause 3, wherein the stretched portion of the tubing forms at least one of a y-shape or an umbrella shape corresponding to a shape of the portion of the outer surface of the body at the intermediate portion which defines a cross-sectional width that tapers from the head portion to the base portion of the body.

Clause 6: The tubing junction assembly of Clause 5, wherein a proximal end of the tubing is sandwiched and axially compressed between an upper surface of the head portion of the collar and a lower surface of the head portion of the body.

Clause 7: The tubing junction assembly of Clause 6, wherein the upper surface of head portion of the collar is solvent bonded to the lower surface of the head portion of the body.

Clause 8: The tubing junction assembly of Clause 6, wherein the upper surface of head portion of the collar is ultraviolet (UV) adhesive bonded to the lower surface of the head portion of the body.

Clause 9: The tubing junction assembly of Clause 6, wherein the upper surface of head portion of the collar is ultrasonically welded to the lower surface of the head portion of the body.

Clause 10: The tubing junction assembly of Clause 6, wherein the upper surface of head portion of the collar is snap fit coupled to the lower surface of the head portion of the body.

Clause 11: The tubing junction assembly of Clause 6, wherein the upper surface of head portion of the collar is threaded to the lower surface of the head portion of the body.

Clause 12: The tubing junction assembly of Clause 1, wherein the tubing comprises a chemical-inert, solvent-inert or adhesive-inert tubing.

Clause 13: The tubing junction assembly of Clause 1, wherein the tubing comprises a non-polyvinyl chloride (PVC) tubing.

Clause 14: The tubing junction assembly of Clause 8, wherein the tubing comprises a thermoplastic elastomer (TPE) tubing.

Clause 15: A method of forming a tubing junction assembly, the method comprising: providing a body including a head portion, a base portion extending longitudinally from the head portion, the body having an outer surface, a proximal end portion, a distal end portion and an intermediate portion interposed between the proximal end portion and the distal end portion, wherein at least a portion of the outer surface of the body at the intermediate portion defines a cross-sectional width that tapers from the head portion to the base portion; sleeving a tubing over the outer surface of the body and stretching a proximal end portion of the tubing over at least a portion of the outer surface of the body at the intermediate portion to form at least one of a y-shape or an umbrella-shape; sleeving a collar over the tubing such that the tubing is interposed between the collar and the body, the collar having a head portion, a base portion extending longitudinally from the base portion, and an inner surface defining a passage that extends between the head portion and the base portion; and connecting a lower surface of the head portion of the body to an upper surface of the of the head portion of the collar such that a proximal end of the y-shape or umbrella-shape proximal end portion tubing is sandwiched and compressed between the body and the collar.

Clause 16: The method of Clause 15, wherein sleeving the tubing over the outer surface of the body comprises sleeving the tubing over the outer surface with an interference fit, and sleeving the collar over the tubing comprises press-fitting the collar over at least a portion of the tubing.

Clause 17: The method of Clause 15, wherein connecting the lower surface of the head portion of the body to the upper surface of the of the head portion of the collar comprises solvent bonding the lower surface of the head portion of the body to the upper surface of the of the head portion of the collar.

Clause 18: The method of Clause 15, wherein connecting the lower surface of the head portion of the body to the upper surface of the of the head portion of the collar comprises ultraviolet (UV) adhesive bonding the lower surface of the head portion of the body to the upper surface of the of the head portion of the collar.

Clause 19: The method of Clause 15, wherein connecting the lower surface of the head portion of the body to the upper surface of the of the head portion of the collar comprises ultrasonically welding the lower surface of the head portion of the body to the upper surface of the of the head portion of the collar.

Clause 20: The method of Clause 15, wherein connecting the lower surface of the head portion of the body to the upper surface of the of the head portion of the collar comprises snap fitting the lower surface of the head portion of the body to the upper surface of the of the head portion of the collar.

Clause 21: The method of Clause 15, wherein connecting the lower surface of the head portion of the body to the upper surface of the of the head portion of the collar comprises threading the lower surface of the head portion of the body to the upper surface of the of the head portion of the collar.

Clause 22: The method of Clause 15, wherein sleeving the tubing over the outer surface of the body comprises sleeving at least one of a chemical-inert, solvent-inert or adhesive-inert tubing over the outer surface of the body.

FURTHER CONSIDERATIONS

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neutral gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear," "upper," "lower," and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A tubing junction assembly comprising:
   a body including a head portion and a base portion extending longitudinally from the head portion, the body having an outer surface, the head portion defining a proximal end portion of the body, the base portion defining a distal end portion and an intermediate portion interposed between the proximal end portion and the distal end portion of the body, wherein at least a portion of the outer surface of the body at the intermediate portion defines a diameter that decreases from the head portion to the base portion; and
   a collar coupled to the body, the collar having a head portion, a base portion extending longitudinally from the head portion, and an inner surface defining a passage that extends between the head portion and the base portion, the head portion comprising a proximal end portion and a distal end portion, and the inner surface at the head portion of the collar defines a diameter that decreases from the proximal end portion to the distal end portion of the head portion, wherein the diameter of the outer surface of the body along the intermediate portion is approximately equal to the diameter of the inner surface of the head portion of the collar, wherein a tubing having a proximal end portion, a distal end portion, an outer surface, and an inner surface defining a lumen extending from the proximal end portion to the distal end portion is stretched over the outer surface of the body with the proximal end portion of the tubing stretched over at least a portion of the outer surface of the body at the intermediate portion, and wherein the inner surface of the collar is sleeved over at least a portion of the outer surface of the tubing and coupled to the collar such that the proximal end portion of the tubing is compressed between the body and the collar.

2. The tubing junction assembly of claim 1, wherein the lumen of the tubing has a diameter approximately equal to a cross-sectional width of the outer surface of the body at the base portion in an unstretched state of the tubing such that the tubing is sleeved over the outer surface of the body with an interference fit.

3. The tubing junction assembly of claim 2, wherein the inner surface at the base portion of the collar has a cross-sectional width approximately equal to a sum of the cross-sectional width of the outer surface of the body at the base portion and a thickness of the tubing sleeved over the outer surface of the body at the base portion such that the collar is sleeved over the outer surface of the tubing with an interference fit to radially compress the tubing.

4. The tubing junction assembly of claim 3, wherein the stretched portion of the tubing forms at least a flared shape corresponding to a shape of the portion of the outer surface of the body at the intermediate portion.

5. The tubing junction assembly of claim 4, wherein a proximal end of the tubing is sandwiched and axially compressed between an upper surface of the head portion of the collar and a lower surface of the head portion of the body.

6. The tubing junction assembly of claim 5 wherein the upper surface of the head portion of the collar is solvent bonded to the lower surface of the head portion of the body.

7. The tubing junction assembly of claim 5, wherein the upper surface of head portion of the collar is ultraviolet adhesive bonded to the lower surface of the head portion of the body.

8. The tubing junction assembly of claim 5, wherein the upper surface of head portion of the collar is ultrasonically welded to the lower surface of the head portion of the body.

9. The tubing junction assembly of claim 1, wherein the tubing comprises a chemical-inert, solvent-inert or adhesive-inert tubing.

10. The tubing junction assembly of claim 1, wherein the tubing comprises a non-polyvinyl chloride tubing.

11. The tubing junction assembly of claim 10, wherein the tubing comprises a thermoplastic elastomer tubing.

12. The tubing junction assembly of claim 1, wherein connecting a lower surface of the head portion of the body to an upper surface of the of the head portion of the collar comprises axially compressing and radially compressed the tubing between the body and the collar.

13. A method of forming a tubing junction assembly, the method comprising:
providing a body including a head portion and a base portion extending longitudinally from the head portion, the body having an outer surface, the head portion defining a proximal end portion of the body, the base portion defining a distal end portion and an intermediate portion interposed between the proximal end portion and the distal end portion of the body, wherein at least a portion of the outer surface of the body at the intermediate portion defines a body diameter that decreases from the head portion to the base portion;
sleeving a tubing over the outer surface of the body and stretching a proximal end portion of the tubing over at least a portion of the outer surface of the body at the intermediate portion to form at least a flared shape along the proximal end portion of the tubing;
sleeving a collar over the tubing such that the tubing is interposed between the collar and the body, the collar having a head portion, a base portion extending longitudinally from the head portion, and an inner surface defining a passage that extends between the head portion and the base portion, wherein the inner surface along the head portion of the collar defines a collar diameter that decreases along the head portion and is approximately equal to the body diameter along the intermediate portion; and
connecting a lower surface of the head portion of the body to an upper surface of the of the head portion of the collar such that the flared shape along the proximal end portion of the tubing is compressed between the body and the collar.

14. The method of claim 13, wherein sleeving the tubing over the outer surface of the body comprises sleeving the tubing over the outer surface with an interference fit, and sleeving the collar over the tubing comprises press-fitting the collar over at least a portion of the tubing.

15. The tubing junction assembly of claim 13, wherein connecting the lower surface of the head portion of the body to the upper surface of the of the head portion of the collar comprises any of solvent bonding and ultraviolet adhesive bonding the lower surface of the head portion of the body to the upper surface of the of the head portion of the collar.

16. The method of claim 13, wherein connecting the lower surface of the head portion of the body to the upper surface of the of the head portion of the collar comprises ultrasonically welding the lower surface of the head portion of the body to the upper surface of the of the head portion of the collar.

17. The method of claim 13, wherein connecting the lower surface of the head portion of the body to the upper surface of the of the head portion of the collar comprises any of snap fitting and threading the lower surface of the head portion of the body to the upper surface of the of the head portion of the collar.

18. The method of claim 13, wherein sleeving the tubing over the outer surface of the body comprises sleeving at least one of a chemical-inert, solvent-inert or adhesive-inert tubing over the outer surface of the body.

19. The tubing junction assembly of claim 13, wherein the tubing is axially compressed and radially compressed between the body and the collar.

* * * * *